United States Patent [19]

Green et al.

[11] Patent Number: 4,632,290
[45] Date of Patent: Dec. 30, 1986

[54] SURGICAL STAPLER APPARATUS

[75] Inventors: David T. Green, Norwalk; Douglas G. Noiles, New Canaan, both of Conn.

[73] Assignee: United States Surgical Corporation, Norwalk, Conn.

[21] Appl. No.: 293,111

[22] Filed: Aug. 17, 1981

[51] Int. Cl.⁴ ............................................. A61B 17/10
[52] U.S. Cl. .................................. 227/19; 227/155; 227/DIG. 1; 128/334 R
[58] Field of Search .................. 128/334 R, 334 C; 227/DIG. 1, 61, 62, 77, 19, 155

[56] References Cited

U.S. PATENT DOCUMENTS

| 2,631,284 | 3/1953 | Pfyffer | 1/13.5 |
|---|---|---|---|
| 3,079,608 | 3/1963 | Babkin | 1/187 |
| 3,080,564 | 3/1963 | Strekopitov et al. | 227/DIG. 1 X |
| 3,458,099 | 7/1969 | Schick | 227/111 |
| 3,494,533 | 2/1970 | Green et al. | 227/19 |
| 3,499,591 | 3/1970 | Green | 227/76 |
| 3,606,888 | 9/1971 | Wilkinson | 128/334 |
| 3,673,671 | 7/1972 | Petersen | 29/432.2 |
| 3,836,061 | 9/1974 | Grunwald | 227/155 |
| 3,871,227 | 3/1975 | Tidwell, Jr. | 72/476 |
| 3,981,425 | 9/1976 | Megumi | 227/155 |
| 4,181,327 | 1/1980 | Merrill | 281/25 R |
| 4,305,539 | 12/1981 | Korolkov et al. | 227/8 |

FOREIGN PATENT DOCUMENTS

499619  5/1930  Fed. Rep. of Germany .
1339394 12/1973  United Kingdom .

Primary Examiner—Michael H. Thaler
Attorney, Agent, or Firm—Thomas R. Bremer

[57] ABSTRACT

An improved anvil for crimping or clinching generally U-shaped surgical staples in a surgical stapler includes a main channel transverse to the bases of the staples, the bottom surface of the main channel being the staple crimping or clinching surface and having a plurality of closely spaced grooves or secondary channels transverse to the longitudinal axis of the main channel for allowing staples to be crimped or clinched at substantially any location along the length of the main channel.

12 Claims, 36 Drawing Figures

SURGICAL STAPLER APPARATUS

BACKGROUND OF THE INVENTION

This invention relates to surgical staplers, and more particularly to improved anvils for use in surgical staplers of the type in which one or more U-shaped surgical staples are driven through body tissue and against an anvil to deflect, crimp, or clinch the ends of the staple legs and thereby secure the tissue.

Surgical staplers having a wide variety of configurations are known. This invention relates to the general type of surgical staplers in which the tissue to be stapled is positioned between a staple holding assembly and an opposing anvil assembly, and one or more generally U-shaped staples are driven from the staple holding assembly, through the tissue, and against the anvil to deflect, crimp, or clinch the ends of the legs of the staples and secure the tissue. (In relation to forming a staple, the words "deflect", "crimp", and "clinch" are used interchangeably herein to refer to deformation of the staple by the anvil.) Examples of this general type of surgical stapler are the linear closure staplers shown in Green et al. U.S. Pat. No. 3,494,533, the circular anastomosis staplers shown in Conta et al. U.S. Pat. No. 4,304,236 and the linear anastomosis staplers shown in Green U.S. Pat. No. 3,499,591.

In staplers of the general type described above, it is conventional to provide separate anvil slots at each staple forming location. This makes it necessary to maintain relatively stringent alignment between the staple holding assembly and the anvil to assure that the staples enter the anvil slots correctly for proper crimping or clinching. It is extremely important that every staple be formed properly, because any incompletely or improperly formed staple can leave a gap in a wound closure, with the possibility of such adverse consequences as improper or prolonged healing of the wound or leakage of blood or other body fluid or body contents through the wound. The necessity of maintaining a high degree of alignment between the relatively movable staple holding assembly and anvil assembly may contribute significantly to the complexity of the instrument and to the cost of manufacturing and maintaining it.

In view of the foregoing, it is an object of this invention to improve and simplify surgical staplers of the type described above.

It is a more particular object of this invention to substantially eliminate at least some of the requirements for exact alignment in surgical staplers of the type described above.

SUMMARY OF THE INVENTION

These and other objects of the invention are accomplished in accordance with the principles of the invention by providing surgical staplers in which the staple crimping surface of the anvil assembly comprises at least one main channel having a longitudinal axis transverse to the longitudinal axis of the base of the U-shaped staples to be crimped. The length of the main channel parallel to its longitudinal axis is at least several times the cross sectional dimension of the wire from which the staples are made. The main channel is scored or grooved transverse to its longitudinal axis with a plurality of closely spaced, substantially parallel grooves or subordinate secondary channels. The cross sectional dimensions of each secondary channel are substantially smaller than the cross sectional dimensions of the main channel, but each secondary channel is sufficiently prominent to guide the ends of a staple substantially parallel to the secondary channel. The grooved main channel therefore constitutes a substantially continuous staple forming surface of substantial longitudinal extent against which the legs of a staple can be driven and clinched at any location along the longitudinal axis of the main channel. Alignment of the staple holding assembly and the anvil assembly in the direction parallel to the longitudinal axis of the main channel is therefore no longer critical.

Although the longitudinal axis of the main channel may be substantially perpendicular to the longitudinal axis of the base of the staple, and although the secondary channels may be substantially perpendicular to the longitudinal axis of the main channel, either or both of these relationships may be other than perpendicular. Typically, the angle between the longitudinal axis of the staple base and the secondary channels is in the range from 0° to 45°, preferably in the range from 0° to 30°. Thus the anvils of this invention can be used to skew the ends of the staple during formation, as is desirable in a number of applications of the invention.

In the case of circular anastomosis surgical staplers, the main channel can be a closed circular loop, and the need for rotational alignment between the staple holding assembly and the anvil can be entirely eliminated.

Other objects of the invention, its nature and various advantages will be more apparent from the accompanying drawing and the following detailed description of the invention.

BRIEF DESCRIPTION OF THE DRAWING

FIGS. 17 and 18 are views taken in opposite directions so that in actual practice the apparatus of FIG. 18 faces toward the apparatus of FIG. 17. Also as in the previously depicted embodiments, FIGS. 19 and 20 are taken in the same direction as FIG. 17, which is opposite the direction in which FIG. 18 is taken.

FIG. 35 is taken along the line 35—35 in FIG. 36.

DETAILED DESCRIPTION OF THE INVENTION

Figure 1:
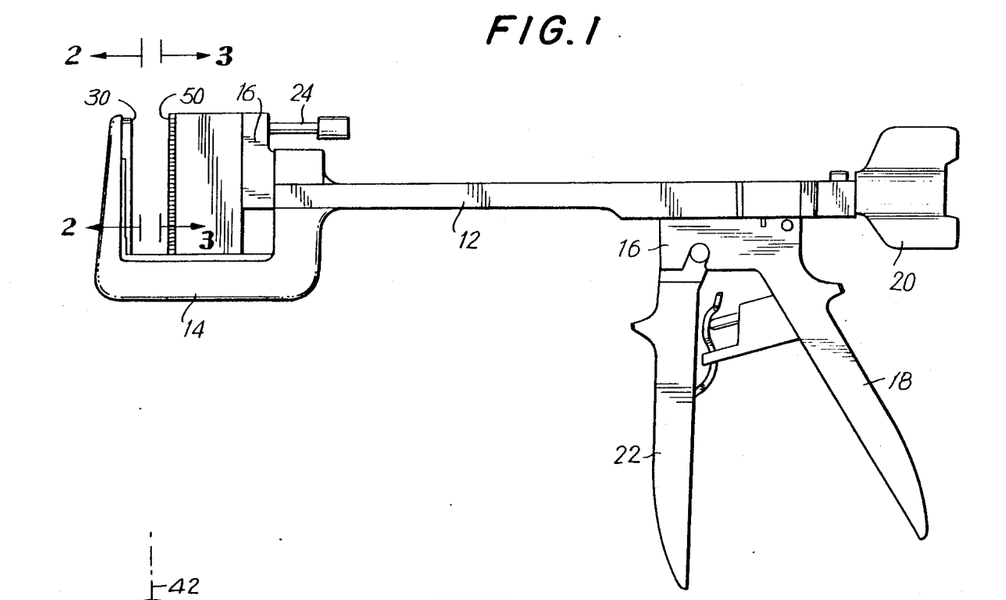
FIG. 1 is a simplified elevational view of a linear closure surgical stapler employing the improved anvil of this invention.
Figure 2:
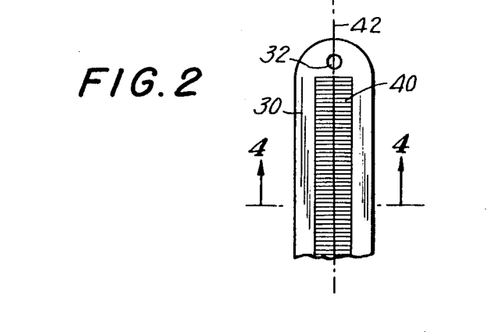
FIG. 2 is a partial sectional view taken along the line 2—2 in FIG. 1.
Figure 3:
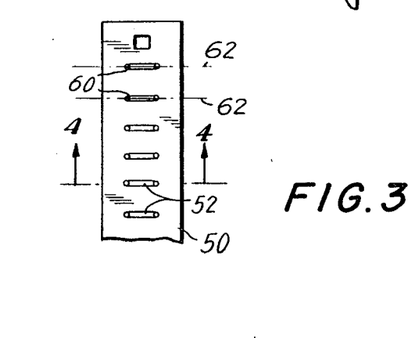
FIG. 3 is a partial sectional view taken along the line 3—3 in FIG. 1.

FIG. 1 illustrates a typical linear closure surgical stapler of the type shown, for example, in Green et al. U.S. Pat. No. 3,494,533. The particular configuration of the stapler is not critical to the present invention, and the stapler shown serves only to illustrate one possible environment for the invention.

As is now well known to those skilled in the art, the linear closure staper shown in FIG. 1 includes a longitudinal frame 12 having a square-cornered U-shaped distal end portion 14. Anvil 30 is mounted on the distal leg of distal end portion 14. Reciprocally mounted within frame 12 is a longitudinal staple holding assembly support 16, which includes at its proximal end fixed handle 18, and which supports staple holding assembly 50 at its distal end. The proximal end of support 16 also includes a proximally extending screw (not visible) which extends into and threadedly engages wing nut 20. Wing nut 20 is rotatably mounted on the distal end of frame 12. When wing nut 20 is rotated, the threaded connection between wing nut 20 and support 16 causes support 16 to translate longitudinally relative to frame 12. Staple holding assembly 50 is thereby moved toward or away from anvil 30 to respectively clamp or release tissue (not shown) positioned between elements 30 and 50.

Handle 22 is pivotally mounted on support 16. When handle 22 is pivoted toward fixed handle 18, it reciprocates a staple pusher bar (not shown) in support 16. This staple pusher bar actuates a staple pusher mechanism including pusher fingers 54 (FIGS. 5 and 6) in staple holding assembly 50 to drive a plurality of staples 60 (FIGS. 3-6) from staple guides 52 in the staple holding assembly, through tissue clamped between the opposing faces of anvil 30 and assembly 50, and against anvil 30. Anvil 30 crimps or clinches the ends of the staples to secure or staple the tissue. Before the staples are driven, pin 24 is pushed through assembly 50 and into an aperture 32 in anvil 30 to confine the tissue to be stapled within the stapling space and to help align assembly 50 and anvil 30.

Figure 4:
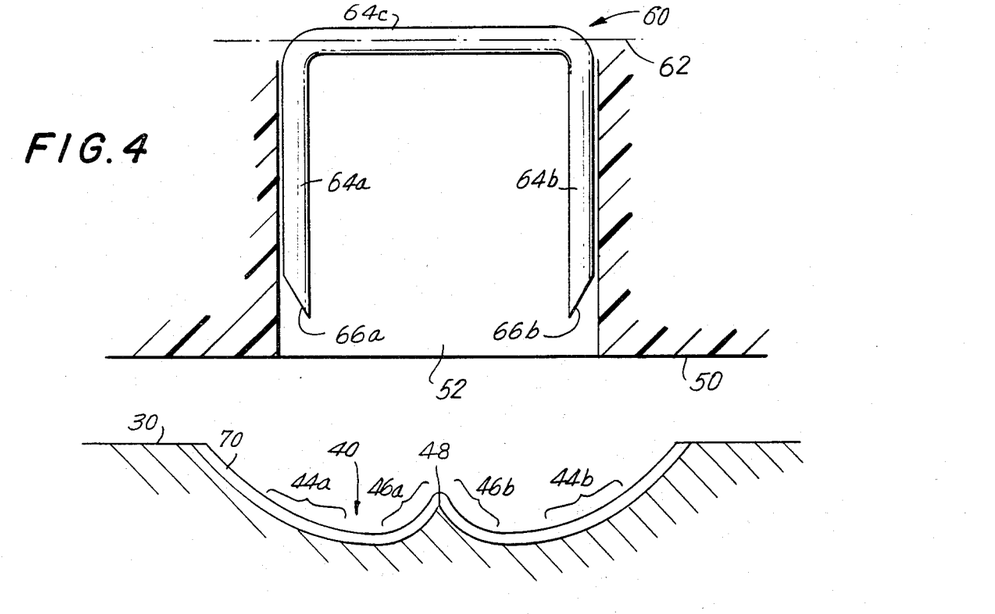
FIG. 4 is an enlarged sectional view taken along the line 4—4 in FIGS. 2 and 3 showing a typical surgical staple in position for driving against the anvil.

As is best seen in FIG. 4, each staple 60 is typically preformed in the shape of a square cornered U. Each staple includes two initially straight, substantially parallel legs 64a and 64b which are joined together at one end by the base 64c of the staple. Legs 64a and 64b are typically at right angles to base 64c, and the free ends 66a and 66b of legs 64a and 64b are typically sharply pointed to facilitate penetration of the tissue to be stapled. Staple 60 is typically made of round metal wire, although other cross sectional shapes such as square or rectangular shapes are possible and are within the scope of this invention.

Although not necessary to an understanding of the present invention, additional information regarding the construction and operation of linear closure staplers of the type shown in FIG. 1 and described above will be found in Green et al. U.S. Pat. No. 3,494,533.

In accordance with the present invention, the staple crimping or clinching surface of anvil 30 (FIGS. 2 and 4-8) comprises a main channel 40 having a longitudinal axis 42 transverse to the longitudinal axes 62 of the bases of the staples 60 to be clinched. Although in the particular embodiment shown in FIGS. 1-8 the longitudinal axis 42 of main channel 40 is substantially perpendicular to the longitudinal axes 62 of the staple bases, this is not necessarily the case as will be shown in relation to several of the alternative embodiments discussed below. Thus the word "transverse" is used herein and in the appended claims in regard to the relationship between the main channel axis and the staple bases in the general sense of non-parallel, crossing, or intersecting, and is not limited to an exactly perpendicular relationship.

Figure 5:
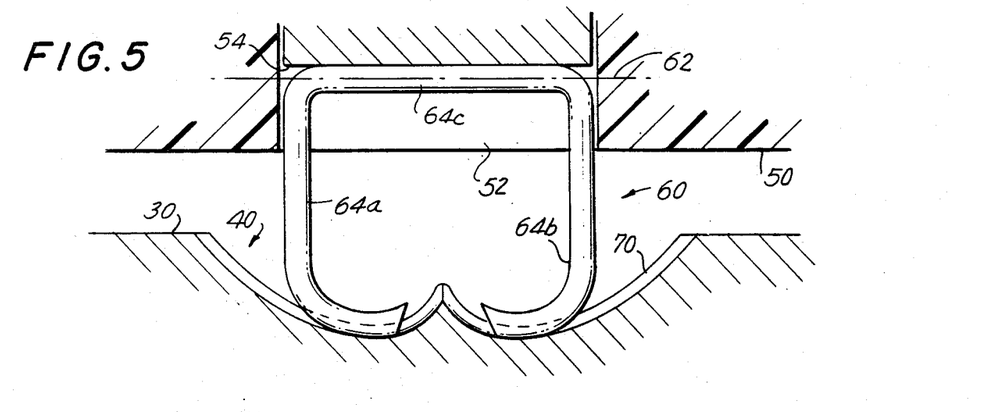
FIG. 5 is a view similar to FIG. 4 showing an intermediate stage in the driving of the staple against the anvil.
Figure 6:
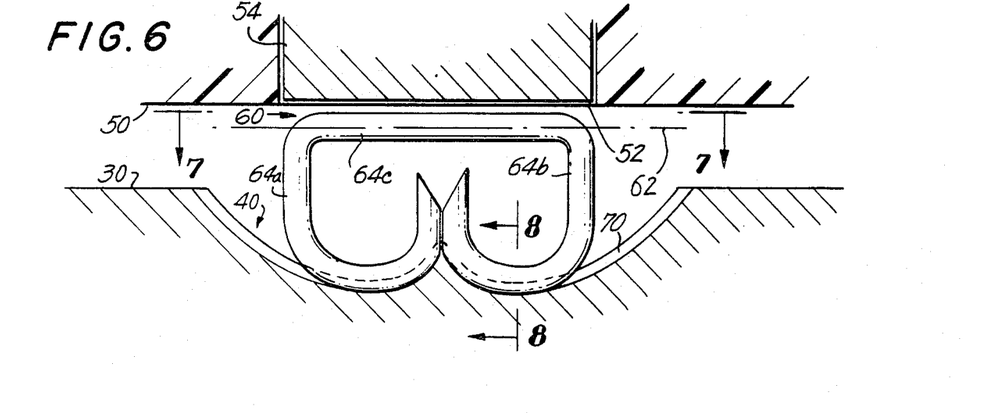
FIG. 6 is another view similar to FIG. 4 showing the final stage in the driving of the staple against the anvil.
Figure 7:
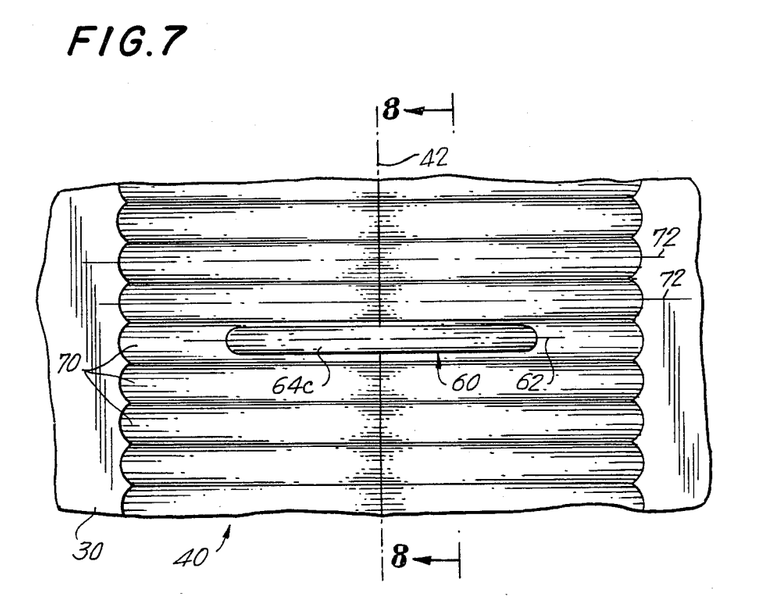
FIG. 7 is an elevational view taken along the line 7—7 in FIG. 6.
Figure 8:
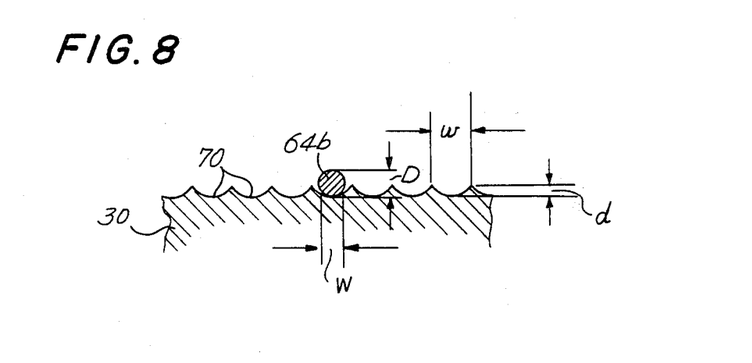
FIG. 8 is a sectional view taken along the line 8—8 in FIG. 6 or FIG. 7.

The bottom of main channel 40 is shaped to promote bending of staple legs 64a and 64b in the desired manner when the staple is driven against the anvil. In the particular embodiment shown in FIGS. 2 and 4-8 it is desired to produce a finished staple having the B shape best seen in FIG. 6. Thus the bottom of main channel 40 is shaped so that the portions 44a and 44b initially contacted by the ends of staple legs 64a and 64b slope away from the ends of the staple legs in the direction toward the center of the main channel. Accordingly, when staple 60 is driven toward anvil 30, the ends of staple legs 64a and 64b bend inwardly toward one another as best seen in FIG. 5. Toward the center of main channel 40 in the region designated 46a and 46b, the bottom surface of the channel curves upward toward the base 64c of the staple so that the legs of the staple are bent back toward the center of base 64c as the staple is driven farther toward the anvil (see FIG. 6). Thus main channel 40 has a central ridge 48 parallel to longitudinal axis 42.

To assure that staple legs 64a and 64b bend in the desired plane (which in the particular embodiment shown in FIGS. 2 and 4-8 is the original plane of the staple), the bottom surface of main channel 40 is scored or grooved to provide a plurality of closely spaced, substantially parallel grooves or subordinate secondary channels 70 transverse to the longitudinal axis 42 of main channel 40. The term "transverse" is again used in this context in the general sense to mean non-parallel, crossing, or intersecting, and is again not limited to a perpendicular relationship.

Although the cross sectional dimensions of secondary channels 70 are much smaller than the corresponding dimensions of main channel 40, each secondary channel 70 is sufficiently prominent to guide the legs of a staple parallel to the longitudinal axis 72 of the secondary channel. Preferably, each secondary channel 70 is at least large enough in cross section to admit a substantial portion of the cross section of a staple leg. Each secondary channel 70 is also preferably not so wide in cross section that it does not assure guidance of a staple leg substantially parallel to the longitudinal axis 72 of the secondary channel. Typically, each secondary channel 70 has depth in cross section (dimension "d" in FIG. 8) in the range from 15% to 50% of the cross sectional dimension of the staple leg measured parallel to the depth of the secondary channel (dimension "D" in FIG. 8). Thus in terms of the illustrative dimensions shown in FIG. 8, "d" is typically in the range from 0.15 D to 0.5 D. Typically, each secondary channel 70 has width in cross section (dimension "w" in FIG. 8) in the range from about 1 to 2 times the cross sectional width of the portion of the staple received in the secondary channel (dimension "W" in FIG. 8). Again, in terms of the illustrative dimensions shown in FIG. 8, "w" is typically in the range from 1.0 W to 2.0 W. When the staple is made of round wire having radius "R" and the cross sectional surface of secondary channel 70 is an arc of a circle having radius "r", another way of stating the foregoing relationships is that "r" is typically in the range from 1.0 R to 2.0 R, preferably in the range from 1.0 R to 1.5 R, and "d" is typically in the range from 0.3 R to 1.0 R.

The foregoing dimensional considerations apply to all of the embodiments shown and described herein and therefore will not be repeated for every other embodiment discussed in detail below.

The presence of many closely spaced secondary channels 70 transverse to main channel 40 effectively allows a staple to be clinched at any position along the length of main channel 40. The location of anvil 30 parallel to longitudinal axis 42 in relation to the locations at which staples are driven from staple holding assembly 50 is no longer critical to proper staple formation. Indeed, the relative locations of anvil 30 and assembly 50 parallel to longitudinal axis 42 are irrelevant as long as all of staples 60 are driven from assembly 50 somewhere along the length of main channel 40. Each staple will always enter one of secondary channels 70 and be guided by that secondary channel during crimping so that the proper finished staple shape will always result.

The virtual elimination of any requirement for precise alignment of anvil 30 relative to staple holding assembly 50 in one dimension (i.e., parallel to longitudinal axis 42) eases clearance and tolerance requirements for many parts of the surgical stapler. This in turn substantially reduces the cost of the apparatus and facilitates manufacture and maintenance of the apparatus.

FIGS. 9-12 illustrate the application of the principles of this invention to circular anastomosis surgical staplers of the general type shown in Conta et al. U.S. Pat. No. 4,304,236 and now well known to those skilled in the art. Once again, the particular configuration of the stapler is not critical to the present invention, and the stapler shown serves only to illustrate one possible environment for the invention.

Figures 9, 10, 11:
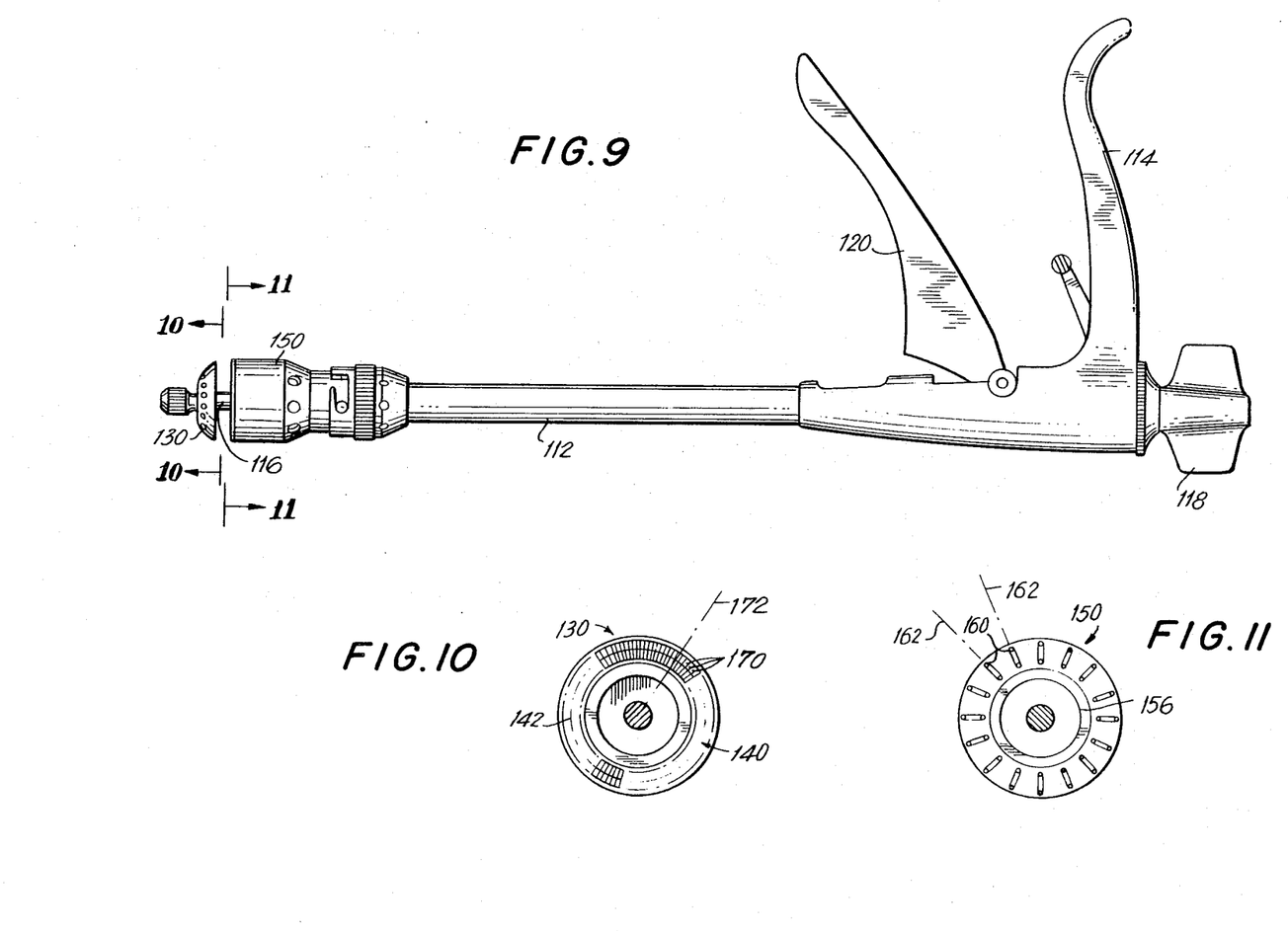
FIG. 9 is a simplified elevational view of a circular anastomosis surgical stapler employing the improved anvil of this invention.
FIG. 10 is a sectional view taken along the line 10—10 in FIG. 9.
FIG. 11 is a sectional view taken along the line 11—11 in FIG. 9.
Figure 12:
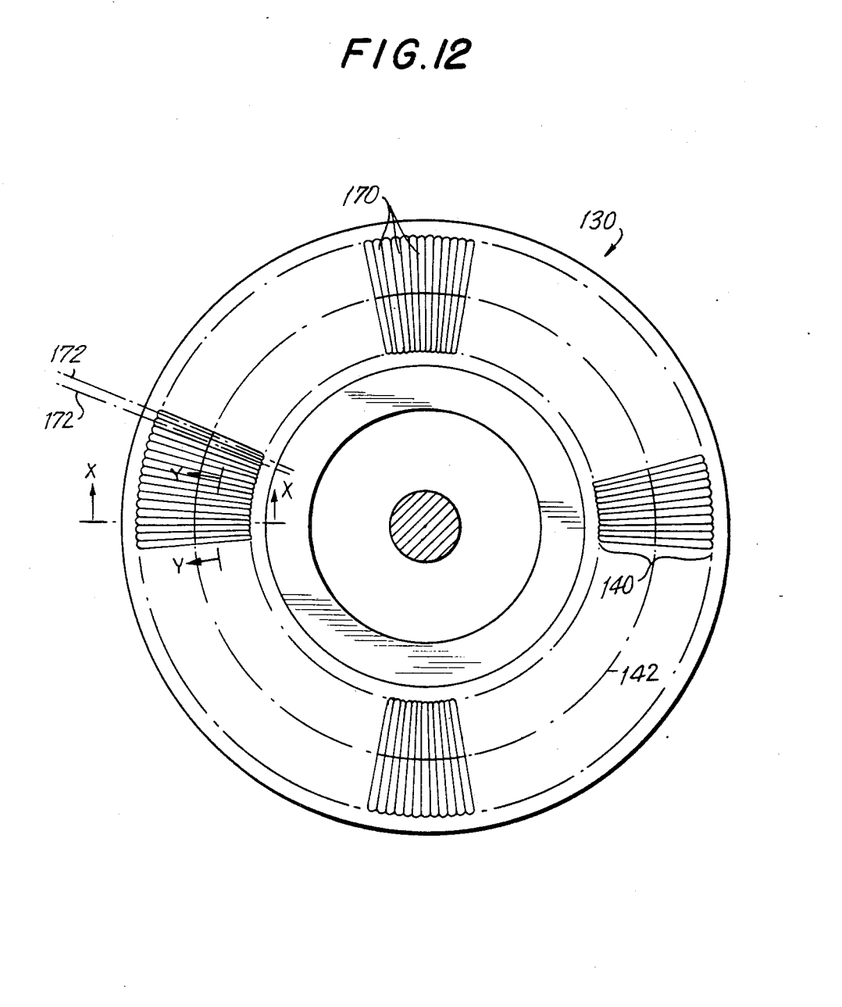
FIG. 12 is an enlarged view similar to FIG. 10.

As shown in FIG. 9, a typical circular anastomosis surgical stapler includes an elongated cylindrical shaft 112 having a fixed handle 114 near the proximal end of the shaft and a staple holding assembly 150 removably mounted on the distal end of the shaft. Coaxially mounted for reciprocation within shaft 112 is an anvil supporting rod 116. Anvil assembly 130 is removably mounted on the distal end of rod 116. The proximal end of rod 116 extends into and is threadedly engaged with wing nut 118, which is rotatably mounted on the proximal end of shaft 112. Rotation of wing nut 118 therefore causes anvil assembly 130 to translate toward or away from the distal face of staple holding assembly 150 to respectively clamp or release tissue (not shown) to be stapled between the opposing faces of assemblies 130 and 150.

Handle 120 is pivotally mounted on shaft 112 adjacent fixed handle 114. Coaxially mounted inside shaft 112 and around rod 116 is a hollow tubular staple driving shaft (not shown). When handle 120 is pivoted toward handle 114, the staple driving shaft inside shaft 112 reciprocates toward staple holding assembly 150 and causes the staple driving mechanism in assembly 150 to eject an annular array of staples 160 (each similar to staples 60 in the embodiment of FIGS. 1-8). The legs of staples 160 pass through the tissue clamped between anvil 130 and staple holding assembly 150 and are crimped or clinched by anvil 130 to secure or staple the tissue. Also included in staple holding assembly 150 is an annular knife 156 (FIG. 11). As the staples are being ejected, annular knife 156 is also driven toward and against anvil assembly 130 to cut away the excess tissue inside the annular array of staples.

A typical use of instruments of the type shown in FIGS. 9-12 is joining the ends of two hollow tubular organ sections, such as sections of the intestines. Shaft 112 is inserted through one organ section so that anvil assembly 130 and a portion of rod 116 extend from the end of the section. Anvil assembly 130 is then inserted in the end of the other organ section. Anvil assembly 130 is reciprocated toward staple holding assembly 150 to clamp the ends of the two organ sections together between the opposing faces of assemblies 130 and 150. The staples are then driven through the clamped tissue to join the two organ sections together by means of an annulus of staples. Any excess tissue inside the annulus of staples is cut away by knife 156. Anvil assembly 130 is then reciprocated away from staple holding assembly 150 to release the stapled tissue and allow removal of the instrument by withdrawal from the organ section surrounding shaft 112.

Although not necessary to an understanding of the present invention, additional information regarding the construction and operation of circular anastomosis surgical staplers of the type shown in FIG. 9 and described above can be found in Conta et al. U.S. Pat. No. 4,304,236.

In the particular embodiment shown in FIGS. 9-12, staples 160 are oriented in staple holding assembly 150 so that the longitudinal axis 162 of the base of each staple 160 is radial with respect to the staple holding assembly (see FIG. 11). The staple clinching surface of anvil assembly 130 comprises an annular main channel 140 opposite the annular array of staples in staple holding assembly 150 FIGS. 10 and 12). Except for being annular, channel 140 has substantially the same shape and features as channel 40 in the embodiment of FIGS. 1–8. Thus a sectional view of anvil 130 taken along the line X—X in FIG. 12 would be substantially identical to any of FIGS. 4–6. Although channel 140 is annular, it will be said to have a longitudinal axis 142 similar to the longitudinal axis 42 of channel 40 in the previously described embodiment. Because channel 140 is annular, longitudinal axis 142 is also annular. Each portion of longitudinal axis 142 is transverse to the longitudinal axis 162 of the base of the adjacent staple 160.

Like channel 40 in the previously discussed embodiment, the bottom of annular main channel 140 is scored or grooved to provide a plurality of closely adjacent grooves or secondary channels 170 transverse to the longitudinal axis 142 of main channel 140. Each of secondary channels 170 has a longitudinal axis 172 which is radial with respect to anvil assembly 130. A sectional view of anvil 130 taken along the line Y—Y in FIG. 12 would be substantially identical to FIG. 8. Similarly, except for the slight divergence of the longitudinal axes 172 of adjacent secondary channnes 170 and the gradual curving of longitudinal axis 142, a further enlargement of any portion of main channel 140 as viewed in FIG. 12 would be substantially identical to FIG. 7. The secondary channels 170 in each portion of main channel 140 are substantially parallel to the longitudinal axis 162 of the base of the adjacent staple 160. Also, although the longitudinal axes 172 of adjacent secondary channels 170 diverge slightly, for convenience herein and in the appended claims these channels will be referred to as substantially parallel to one another.

All of the dimensiona relationships between staple size and secondary channel size discussed above in relation to the embodiment of FIGS. 1–8 apply equally to the embodiment shown in FIGS. 9–12. Thus each secondary channel 170 is sufficiently prominent to guide the legs of a staple parallel to the longitudinal axis 172 of that channel. Preferably, each secondary channel 170 is at least large enough in cross section to admit a substantial portion of the cross section of a staple leg. Each secondary channel 170 is also preferably not so wide in cross section that it does not assure guidance of a staple leg substantially parallel to the longitudinal axis 172 of that secondary channel. The specific relationships discussed above in relation to staple dimensions "D", "W", and "R" on the one hand, and secondary channel dimensions "d", "w", and "r" on the other hand also apply to the embodiment of FIGS. 9–12.

As in the previously discussed embodiment, the present invention substantially eliminates the need for precise alignment between the locations of staples 160 and anvil 130 in the direction parallel to longitudinal axis 142 of main channel 140. In the case of a circular anastomosis stapler as shown in FIGS. 9–12, this means that anvil assembly 130 can have any angular or rotational orientation relative to staple holding assembly 150. It is therefore possible to eliminate from the stapler the previously required means for providing and maintaining a particular angular relationship between anvil assembly 130 and staple holding assembly 150. This substantially simplifies construction, operation, and maintenance of the stapler. The only alignment requirement which remains is the requirement that anvil assembly 130 and staple holding assembly 150 be concentric relative to a common longitudinal axis.

In both of the illustrative embodiments discussed above, the longitudinal axes of the secondary channels are substantially parallel to the longitudinal axes of the bases of the adjacent staples. Accordingly, during crimping of the staples, the secondary channels guide the staple legs so that they remain in the original plane of the staple. This is not necessarily the case, however, and the principles of this invention can be applied to producing finished staples having other shapes, as will now be discussed.

Figure 13:
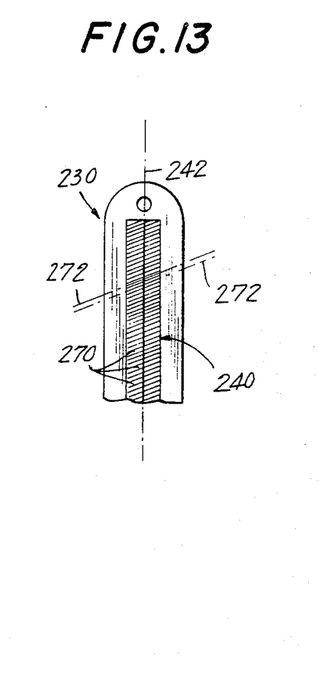
FIGS. 13 and 14 are views respectively of the same general kind as FIGS. 2 and 3 showing an alternative embodiment of the invention.
Figure 14:
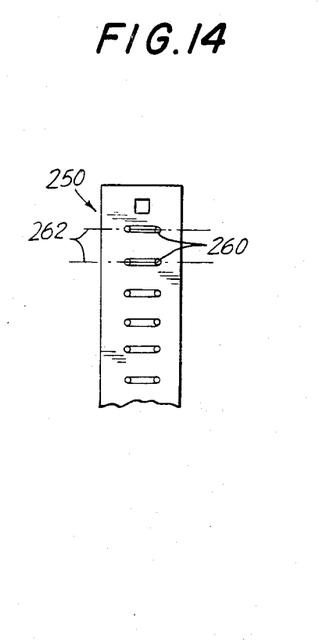

FIG. 13 shows an anvil 230 generally similar to anvil 30 in FIGS. 1–8, except that secondary grooves 270 are not perpendicular to longitudinal axis 242 of main channel 240 (although grooves 270 are still transverse to axis 242). Anvil 230 is used with staple holding assembly 250 (FIG. 14), which is substantially identical to assembly 50 in FIGS. 1–8. Staple holding assembly 250 contains a plurality of U-shaped staples 260 similar to staples 60 in FIGS. 1–8. The longitudinal axis 262 of the base of each staple 260 is substantially perpendicular to longitudinal axis 242. The longitudinal axes 272 of secondary channels 270 therefore form acute angles "A" (FIGS. 15 and 16) with the longitudinal axes 262 of the staple bases. All of axes 262 are substantially parallel, and all of axes 272 are also substantially parallel, so that the acute angle "A" is the same for any pair of axes 262 and 272. For convenience herein, secondary channels such as channels 270 which are not substantially parallel to the base of the adjacent staple are sometimes referred to as skewed.

Figure 15:
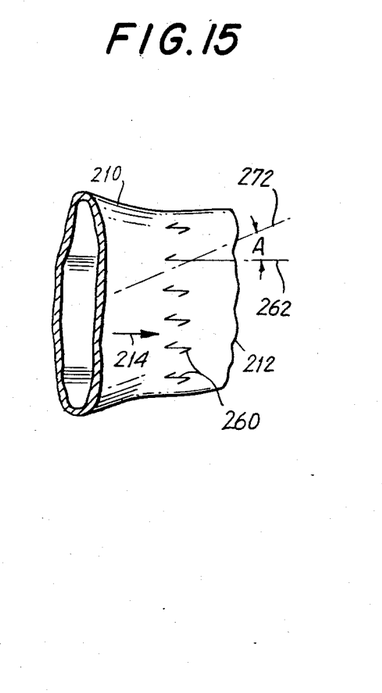
FIG. 15 is a view taken in the same direction as FIG. 13 showing the pattern of finished staples produced in body tissue by the apparatus of FIGS. 13 and 14.
Figure 16:
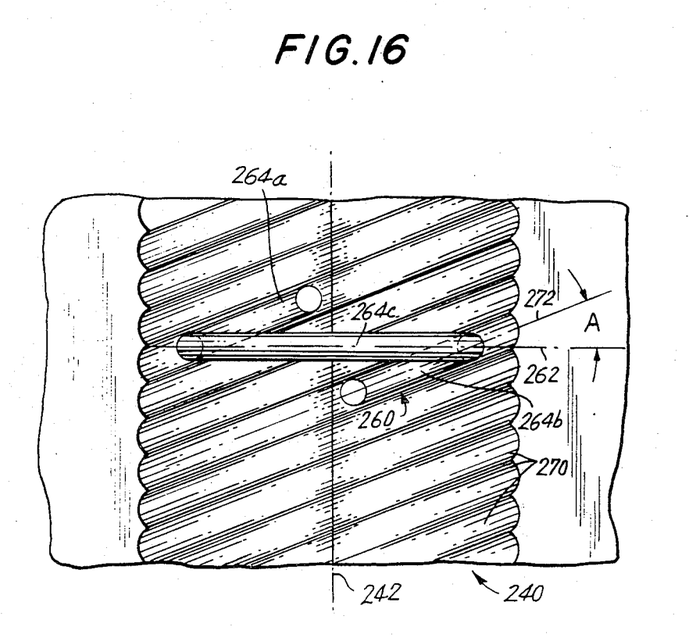
FIG. 16 is a view of the same general kind as FIG. 7, but further illustrating the embodiment of FIGS. 13 and 14.

As in the previously discussed embodiments, secondary channels 270 guide the staple legs substantially parallel to longitudinal axes 272 during crimping of the staples. Accordingly, the effect of skewed secondary channels 270 is to skew the legs of staples 260 during crimping as shown in FIGS. 15 and 16. In particular, the base 264c of each staple remains substantially perpendicular to longitudinal axis 242, but legs 264a and 264b each enter a different one of secondary channels 270 and are guided out of the original plane of the staple as the staple is crimped. When thus crimped, staple leg 264a is angled out from one side of staple base 264c in one direction by an angle "A", while staple leg 264b is angled out from the other side of staple base 264c by an equal and opposite angle "A". Looking down on the finished staples as in FIGS. 15 and 16, each staple has a Z-shaped projection. (FIG. 15 shows a row of finished staples 260 in tissue 210. The staples are shown as though the tissue was transparent so that all of each staple can be seen.) Like secondary channels 270, the legs of each staple 260 are skewed relative to the base of the staple.

As in the previously discussed embodiments, the use of the anvil of this invention having a longitudinal main channel 240 with a plurality of closely spaced transverse secondary channels 270 substantially eliminates the need for precise alignment of the staples and the anvil parallel to the longitudinal axis 242 of the main channel.

The use of skewed staples of the type described above is advantageous in many applications because each such staple tends to exert stapling force on a larger area of tissue. In addition, staples are frequently applied in a row parallel to an incision, and it is usually required that the staples substantially prevent leakage of fluids transverse to the row of staples. In FIG. 15, for example, staples 260 are applied in a row parallel to incision 212, and one of the functions of the staples is to prevent fluid (e.q., air in the case of lung tissue, or the contents of the stomach in the case of stomach tissue) from passing through the row of staples in the direction of arrow 214 and escaping via the incision. The skewed staples distribute the effect of the staples laterally on each side of the base of the staples so that a good barrier to fluid flow transverse to the row of staples is provided without the need for a larger number of more closely spaced staples.

The amount by which the staples are skewed depends on several factors such as stability of the staple during and after formation and the extent to which it is desired to distribute the stapling force laterally of the staple base. Typically, however, the angle "A" of skew is no more than 45° (i.e., in the range from 0° to 45°), preferably no more than 30° (i.e., in the range from 0° to 30°). These skew angle parameters apply to all the skewed staple embodiments described herein and therefore will not be repeated for every such embodiment.

Figure 17:
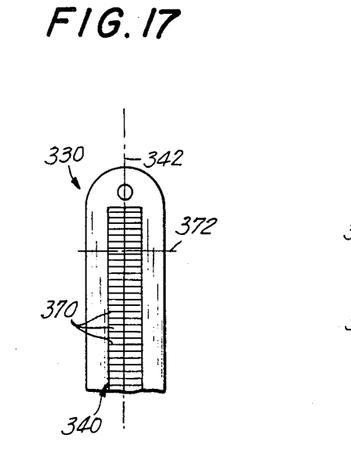
FIGS. 17-20 are views respectively of the same general kind as FIGS. 13-16 showing another alternative embodiment of the invention. As in the previously depicted embodiments.

FIGS. 17–20 show how skewed staples can be produced by skewing the staples rather than the secondary channels of the anvil. As shown in FIG. 17, anvil 330 in this embodiment is substantially identical to anvil 30 in the embodiment of FIGS. 1–8. Accordingly, the longitudinal axes 372 of secondary channels 370 are substantially perpendicular to the longitudinal axis 342 of main channel 340. Staples 360 in staple holding assembly 350, however, are angled or skewed relative to the orientation of staples 60 in the embodiment of FIGS. 1–8. Thus the longitudinal axis 362 of the base of each staple 360 forms an angle "B" with the longitudinal axis 372 of an adjacent secondary channel 370.

Figure 18:
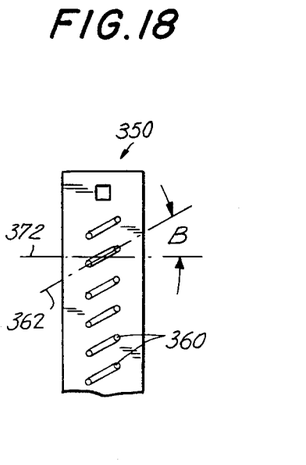
Figure 19:
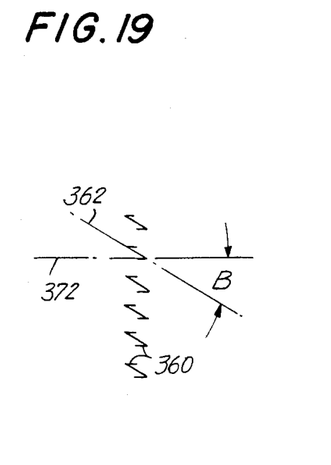
Figure 20:
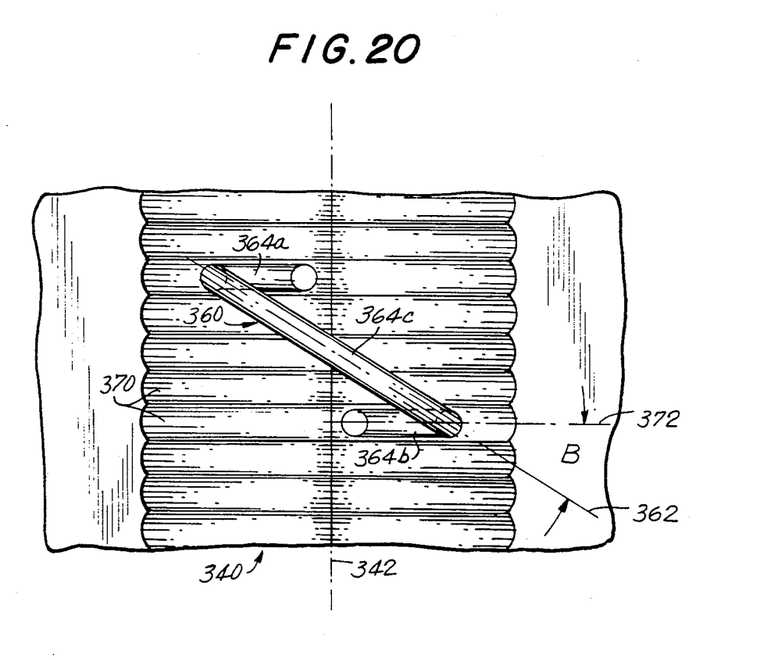
Figure 21:
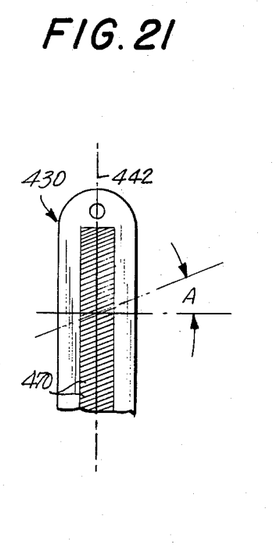
FIGS. 21-24 are views respectively of the same general kind as FIGS. 13-16 showing yet another alternative embodiment of the invention.
Figure 22:
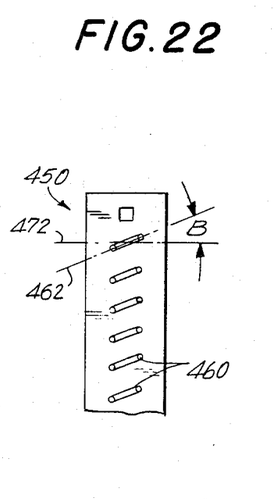

When anvil 330 and staple holding assembly 350 are placed opposite one another (which means that the face of staple holding assembly 350 shown in FIG. 18 is turned over so that it is turned toward the face of anvil 330 shown in FIG. 17) and staples 360 are driven, each leg of each staple enters a different one of secondary channels 370, as best seen in FIG. 20. Each staple leg is guided parallel to the longitudinal axis 372 of the secondary channel it enters. When crimped, staple leg 364a is angled away from one side of staple base 364c by an angle "B", while staple leg 364b is angled away from the other side of staple base 364c by an equal and opposite angle "B". As mentioned above, angle "B" is typically no more than 45°, preferably no more than 30°. A row of finished staples 360 is shown in FIG. 19.

Figure 23:
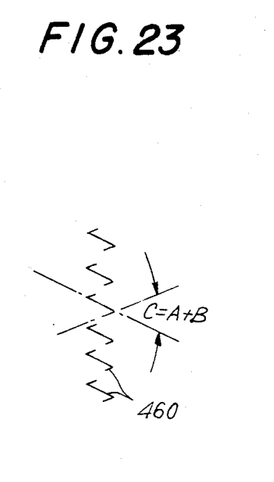
Figure 24:
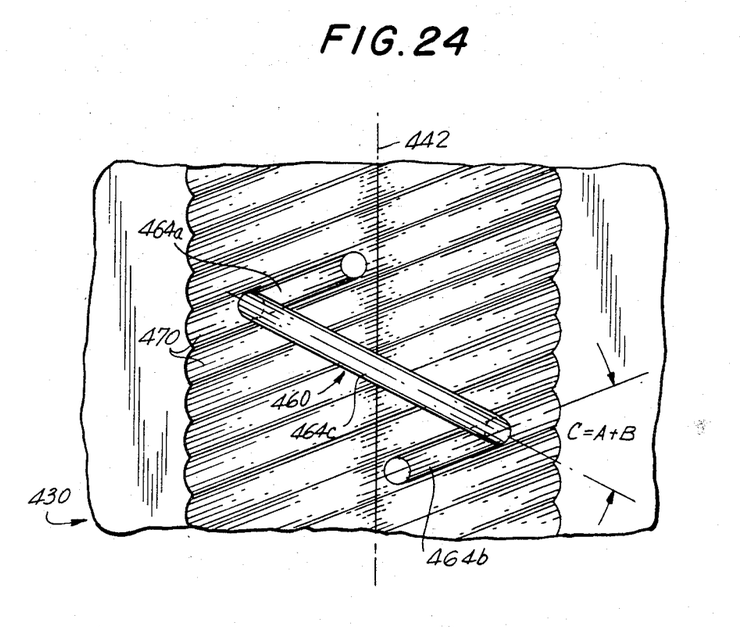
Figure 25:
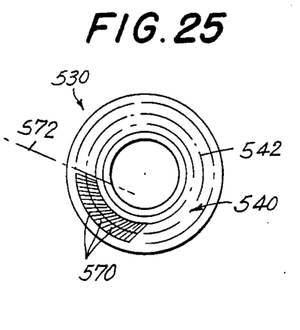
FIGS. 25 and 26 are views respectively of the same general kind as FIGS. 10 and 11 showing still another alternative embodiment of the invention.
Figure 26:
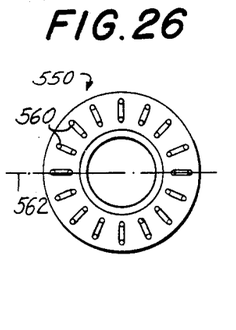

If desired, both the secondary channels and the staple bases can be skewed as shown in FIGS. 21–24 to produce finished staples which are skewed as a result of the combination of both of these effects. Thus anvil 430 in FIG. 21 may be substantially the same as anvil 230 in FIG. 13, and staple holding assembly 450 in FIG. 22 may be substantially the same as assembly 350 in FIG. 18. When staples 460 are crimped against anvil 430, the skewed staple shape shown in FIG. 24 results. The angle "C" between either staple leg 464a or staple leg 464b and staple base 464c is equal to the sum of angles "A" and "B" (respectively similar to the similarly designated angles in the previously discussed embodiments). Angle "C" is typically no more than 45°, preferably no more than 30°. A row of finished staples 460 is shown in FIG. 23 and illustrates how the combination of secondary channel skew and staple base skew produces a row of staples which constitutes a very effective barrier to fluid leakage transverse to the row of staples.

Figure 27:
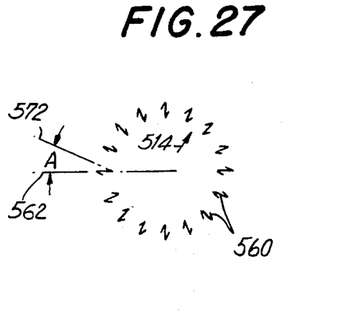
FIG. 27 shows the pattern of finished staples produced in body tissue by the embodiment of FIGS. 25 and 26.
Figure 28:
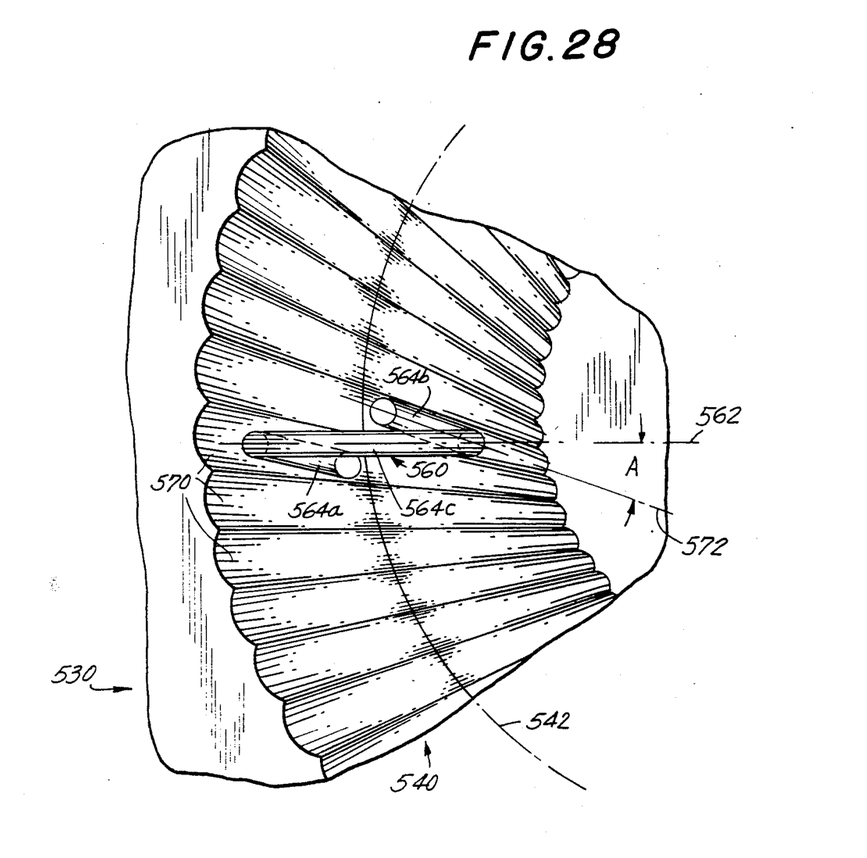
FIG. 28 is an enlarged view of the same general kind as FIG. 16 further illustrating the embodiment of FIGS. 25 and 26.

The principles discussed above relating to skewed staples are also applicable to staplers for providing non-linear closures. Again, the circular anastomosis stapler shown in FIGS. 9–12 is an example of such a non-linear closure stapler. FIGS. 25–28 are respectively comparable to FIGS. 13–16, but for a circular anastomosis stapler of the type shown in FIG. 9. Thus in FIG. 25, annular main channel 540 in anvil 530 has secondary channels 570 which are transverse to, but not perpendicular to, the longitudinal axis 542 of the main channel. The longitudinal axes 572 of secondary channels 570 are therefore non-radial. Staple assembly 550 (FIG. 26) is like staple assembly 150, so that the longitudinal axis 562 of the base of each staple 560 is radial. Accordingly, each secondary channel 570 is skewed relative to the adjacent staple by an angle "A" (FIGS. 27 and 28). When staples 560 are clinched by anvil 530 as best seen in FIG. 28, the legs 564a and 564b of the staples are skewed relative to the staple bases 564c in very much the same way that staples 260 in FIGS. 15 and 16 are formed. As can be seen in FIG. 27, the skewed legs of the staples increase the effectiveness of the annulus of finished staples in preventing fluid leakage transverse to the annulus of staples (e.g., in the direction of arrow 514).

Figure 29:
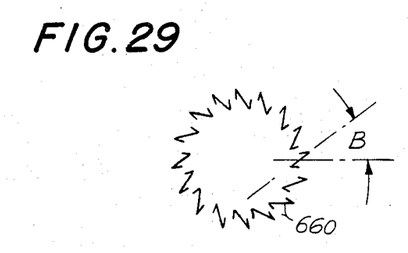
FIG. 29 is a view of the same general kind as FIG. 27 illustrating yet another alternative embodiment of the invention.
Figure 30:
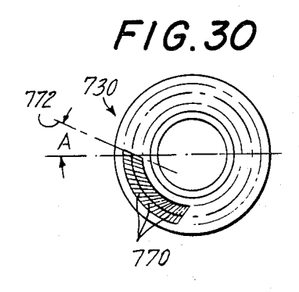
FIGS. 30-33 are views respectively of the same general kind as FIGS. 25-28 showing still another alternative embodiment of the invention.
Figure 31:
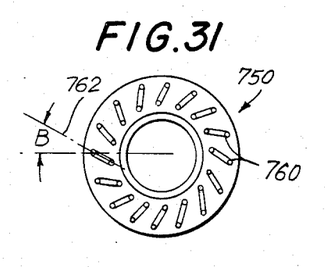

Results similar to those shown in FIG. 27 can alternatively be achieved by having the secondary channels radial and the staples non-radial. This arrangement is analogous to the arrangement shown in FIGS. 17–20. An annulus of staples 660 produced in this way is shown in FIG. 29. The skew angle of staples 660 is the angle "B". This configuration of staples provides a good barrier to transverse fluid leakage, and has the added advantage that the inner diameter of the stapled tissue can be made slightly larger than in FIGS. 10–12 or 27 (all other factors being the same) because the staple bases are non-radial and are therefore effectively smaller in the radial direction. This is desirable to increase the size of the lumen inside the staple annulus.

Figure 32:
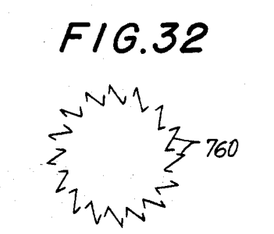
Figure 33:
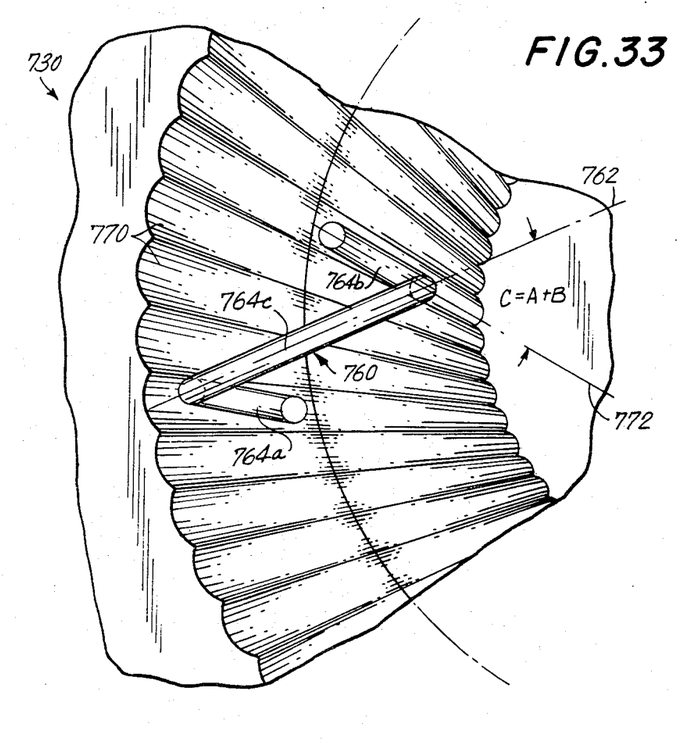

Both of secondary channels and the staples can be non-radical as shown in FIGS. 30–33 to combine the effects described above. Thus in FIG. 30 the secondary channels 770 in anvil 730 are non-radial, and in FIG. 31 staples 760 in staple holding assembly 750 are also non-radial. Accordingly, staple legs 764a and 764b in finished staples 760 (FIGS. 32 and 33) are skewed relative to staple bases 764c by an angle "C", which is approximately equal to the sum of the angle of skew "A" of secondary channels 770 and the angle of skew "B" of the staple bases. The annulus of finished staples produced in this manner is shown in FIG. 32. As in the previously discussed embodiments, angle "C" is typically in the range from 0° to 45°, preferably in the range from 0° to 30°. This arrangement of staples provides both a good barrier to fluid leakage through the annulus of staples and an increased lumen diameter inside the staple annulus.

Figure 34:
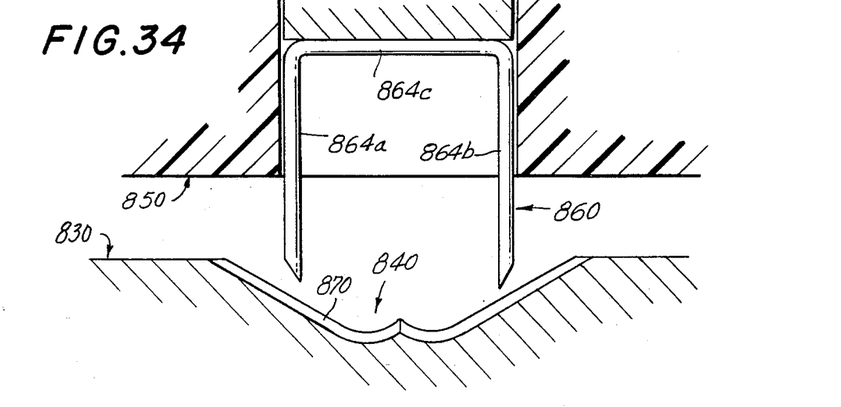
FIG. 34 is a view of the same general kind as FIG. 4 showing another alternative embodiment of the invention.
Figure 35:
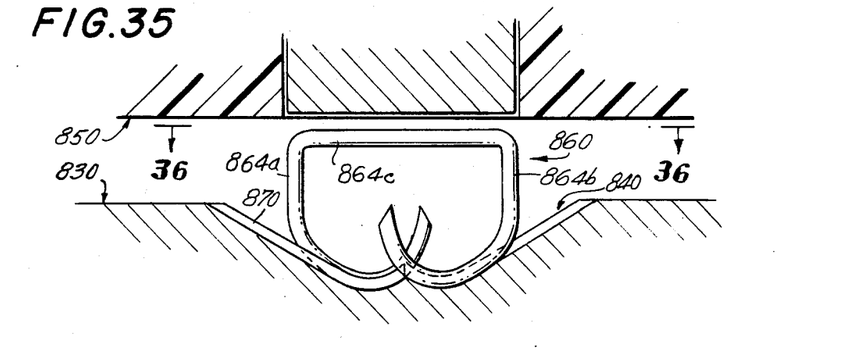
FIG. 35 is a view of the same general kind as FIG. 6 further illustrating the embodiment of FIG. 34.
Figure 36:
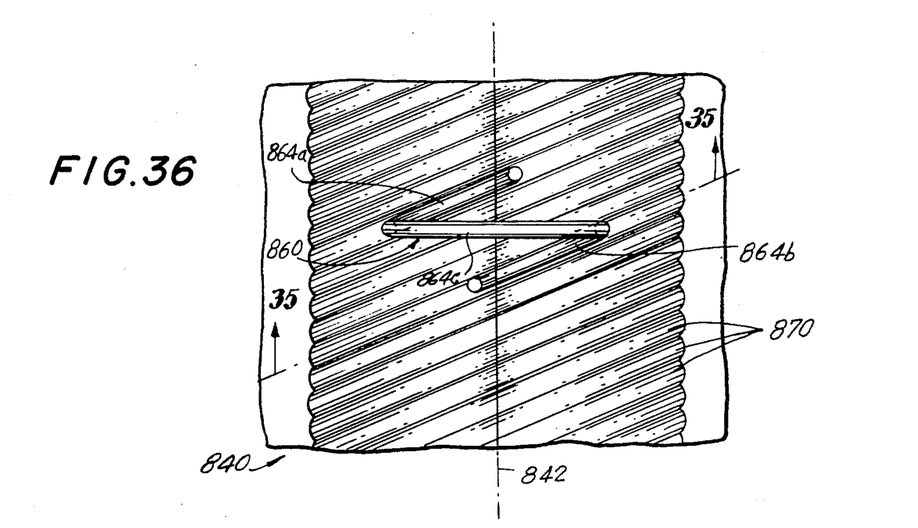
FIG. 36 is an elevational view taken along the line 36—36 in FIG. 35.

Another illustrative finished staple shape is shown in FIGS. 35 and 36. The starting shape of staple 860 (FIG. 34) is substantially the same as in the previously discussed embodiments (although the base 864c of the staple may be somewhat shorter as discussed below). The cross sectional shape of main channel 840 in anvil 830, however, is somewhat modified as compared to the previously discussed embodiments to allow each of staple legs 864a and 864b to cross the centerline or central longitudinal axis 842 of channel 840. Transverse secondary channels 870 are skewed relative to staple base 864c so that staple legs 864a and 864b do not clash or interfere with one another where they cross the centerline of the main channel. One of the advantages of this embodiment of the invention is that it allows the use of staples with shorter staple bases 864c. This may be desirable in such applications as circular anastomosis staplers of the type described above in which the bases of the staples are radial (e.g., FIGS. 25-28) or more nearly radial than circumferential (e.g., FIGS. 29-33 because, for instruments of a given diameter, the shorter staple bases allow a larger lumen to be left inside the annulus of finished staples.

It will be understood that the foregoing is only illustrative of the principles of the invention, and that various modifications can be implemented by those skilled in the art without departing from the scope and spirit of the invention. For example, the various features of the anvil surface can be varied in several respects to produce a wide variety of finished staple shapes, a considerable number of which are illustrated and described above.

We claim:

1. An anvil for clinching the ends of a U-shaped surgical staple in a surgical stapler comprising: a main channel formed in the surface of the anvil and having a longitudinal axis transverse to the longitudinal axis of the base of the U-shaped surgical staple to be clinched against the anvil, the length of the main channel being at least several times greater than the cross sectional dimension of the staple measured parallel to the longitudinal axis of the main channel, the main channel including a plurality of subordinate secondary channels formed in the surface of the main channel, each secondary channel having a longitudinal axis transverse to the longitudinal axis of the main channel and extending lengthwise across the width of the main channel, the secondary channels being laterally immediately adjacent and substantially parallel to one another, the width of each secondary channel being substantially less than the length of the main channel, the depth of each secondary channel measured from the bottom of the main channel to the bottom of the secondary channel being substantially less than the depth of the main channel measured from the top of the main channel to the bottom of the main channel so that all parts of all of the secondary channels, including the boundaries between laterally adjacent secondary channels, are recessed within the main channel, and the width and depth of each secondary channel being great enough to receive and guide the end of the staple substantially parallel to the longitudinal axis of the secondary channel during clinching of the staple.

2. The apparatus defined in claim 1 wherein the longitudinal axis of each secondary channel forms an angle in the range from 0° to 45° with the longitudinal axis of the base of the staple.

3. The apparatus defined in claim 2 wherein the longitudinal axis of each secondary channel forms an angle greater than 0° but no more than 45° with the longitudinal axis of the base of the staple.

4. The apparatus defined in claim 1 wherein the longitudinal axis of each secondary channel forms an angle in the range from 0° to 30° with the longitudinal axis of the base of the staple.

5. The apparatus defined in claim 4 wherein the longitudinal axis of each secondary channel forms an angle greater than 0° but no more than 30° with the longitudinal axis of the base of the staple.

6. The apparatus defined in claim 1 wherein the longitudinal axis of each secondary channel is substantially parallel to the longitudinal axis of the base of the staple.

7. The apparatus defined in claim 1 wherein the longitudinal axis of the main channel is substantially perpendicular to the longitudinal axis of the base of the staple.

8. The apparatus defined in claim 7 wherein the longitudinal axis of each secondary channel is substantially perpendicular to the longitudinal axis of the main channel.

9. The apparatus defined in claim 1 wherein the main channel further includes a centrally located ridge extending parallel to the longitudinal axis of the main channel, each of the two ends of the staple entering the main channel on a respective one of the two sides of the ridge.

10. The apparatus defined in claim 1 wherein the depth of each secondary channel measured from the bottom of the main channel to the bottom of the secondary channel is in the range from 15% to 50% of the thickness of the end of the staple measured substantially perpendicular to the bottom of the secondary channel.

11. The apparatus defined in claim 1 wherein the width of each secondary channel is in the range from 1 to 2 times the width of the portion of the staple received within the secondary channel.

12. The apparatus defined in claim 1 wherein the longitudinal axis of the main channel forms a closed loop.

* * * * *